US011450448B2

United States Patent
Doiron et al.

(10) Patent No.: US 11,450,448 B2
(45) Date of Patent: Sep. 20, 2022

(54) USE OF A LINEAR OCTAFLUOROBUTENE AS A DIELECTRIC COMPOUND IN AN ENVIRONMENTALLY SAFE DIELECTRIC-INSULATION OR ARC-EXTINCTION FLUID

(71) Applicant: HITACHI ENERGY SWITZERLAND AG, Baden (CH)

(72) Inventors: Charles Doiron, Basel (CH); Thomas Alfred Paul, Wädenswil (CH); Branimir Radisavljevic, Zürich (CH); Nitesh Ranjan, Niederrohrdorf (CH); Anna Di-Gianni, Dättwil (CH); Saskia Scheel, Lenzburg (CH)

(73) Assignee: HITACHI ENERGY SWITZERLAND AG, Baden (CH)

( * ) Notice: Subject to any disclaimer, the term of this patent is extended or adjusted under 35 U.S.C. 154(b) by 0 days.

(21) Appl. No.: 16/139,904

(22) Filed: Sep. 24, 2018

(65) Prior Publication Data
US 2019/0027268 A1  Jan. 24, 2019

Related U.S. Application Data

(63) Continuation of application No. PCT/EP2017/056538, filed on Mar. 20, 2017.

(30) Foreign Application Priority Data

Mar. 23, 2016 (WO) ............... PCT/EP2016/056390

(51) Int. Cl.
*H01B 3/24* (2006.01)
*H01B 3/46* (2006.01)
(Continued)

(52) U.S. Cl.
CPC ............... *H01B 3/24* (2013.01); *H01B 3/421* (2013.01); *H01B 3/427* (2013.01); *H01B 3/46* (2013.01);
(Continued)

(58) Field of Classification Search
CPC ............... H01B 3/24; H01B 3/42; H01B 3/46
See application file for complete search history.

(56) References Cited

U.S. PATENT DOCUMENTS 3,033,767 A * 5/1962 Olstowski ................. C25B 3/08
205/356
3,442,942 A * 5/1969 Dario ....................... C09K 5/10
562/850

(Continued)

FOREIGN PATENT DOCUMENTS

| WO | 2010142346 A1 | 12/2010 |
| WO | 2012080246 A1 | 6/2012 |
| WO | 2014037566 A1 | 3/2014 |

OTHER PUBLICATIONS

European Patent Office, International Search Report & Written Opinion issued in corresponding Application No. PCT/EP2017/056538, dated Jun. 19, 2017, 11 pp.
(Continued)

*Primary Examiner* — Liam J Heincer
*Assistant Examiner* — M. Reza Asdjodi
(74) *Attorney, Agent, or Firm* — Sage Patent Group

(57) ABSTRACT

The present invention relates to the use of a linear octafluorobutene as a dielectric compound in an environmentally safe dielectric-insulation or arc-extinction fluid for an apparatus for the generation, the transmission, the distribution and/or the usage of electrical energy.

23 Claims, 1 Drawing Sheet

(51) Int. Cl.
*H01B 3/42* (2006.01)
*H01H 33/22* (2006.01)
*H01B 3/56* (2006.01)
*C07C 19/08* (2006.01)

(52) U.S. Cl.
CPC .............. *H01B 3/56* (2013.01); *H01H 33/22* (2013.01); *C07C 19/08* (2013.01)

(56) References Cited

U.S. PATENT DOCUMENTS

| | | | | |
|---|---|---|---|---|
| 4,175,048 A | * | 11/1979 | Christophorou | H02B 13/055 174/137 B |
| 7,807,074 B2 | * | 10/2010 | Luly | H01B 3/56 252/571 |
| 2002/0045353 A1 | * | 4/2002 | Kang | H01L 21/76897 438/710 |
| 2003/0049460 A1 | * | 3/2003 | O'Neill | C03C 3/045 428/426 |
| 2003/0162034 A1 | * | 8/2003 | O'Neill | H01L 21/316 428/426 |
| 2011/0309715 A1 | * | 12/2011 | Claessens | H01H 11/00 310/273 |
| 2013/0265692 A1 | * | 10/2013 | Mahdizadeh | H02B 1/21 361/601 |
| 2013/0277334 A1 | * | 10/2013 | Mantilla | H01H 33/22 218/85 |
| 2014/0346145 A1 | * | 11/2014 | Piccoz | H01B 3/56 218/90 |
| 2017/0213673 A1 | * | 7/2017 | Elshani | H01H 33/56 |
| 2019/0027268 A1 | * | 1/2019 | Doiron | H01B 3/46 |

OTHER PUBLICATIONS

European Patent Office, International Search Report & Written Opinion issued in corresponding Application No. PCT/EP2016/056390, dated Nov. 21, 2016, 9 pp.

European Patent Office, International Preliminary Report on Patentability issued in corresponding Application No. PCT/EP2017/056538, dated Feb. 26, 2018, 16 pp.

Greenhouse Gas Protocol, Global Warming Potentials, adapted from Table 2.14 of the IPCC Fourth Assessment Report, 2007, <http://www.IPCC.ch>, 5 pages.

Chachereau, A., et al., "Elecron Swarm Parameter Measurements of Perfluorobut-2-ene (2-C4F8)" 32nd ICPIG, Jul. 26-31, 2015, Iasi, Romania, 4 pages.

* cited by examiner

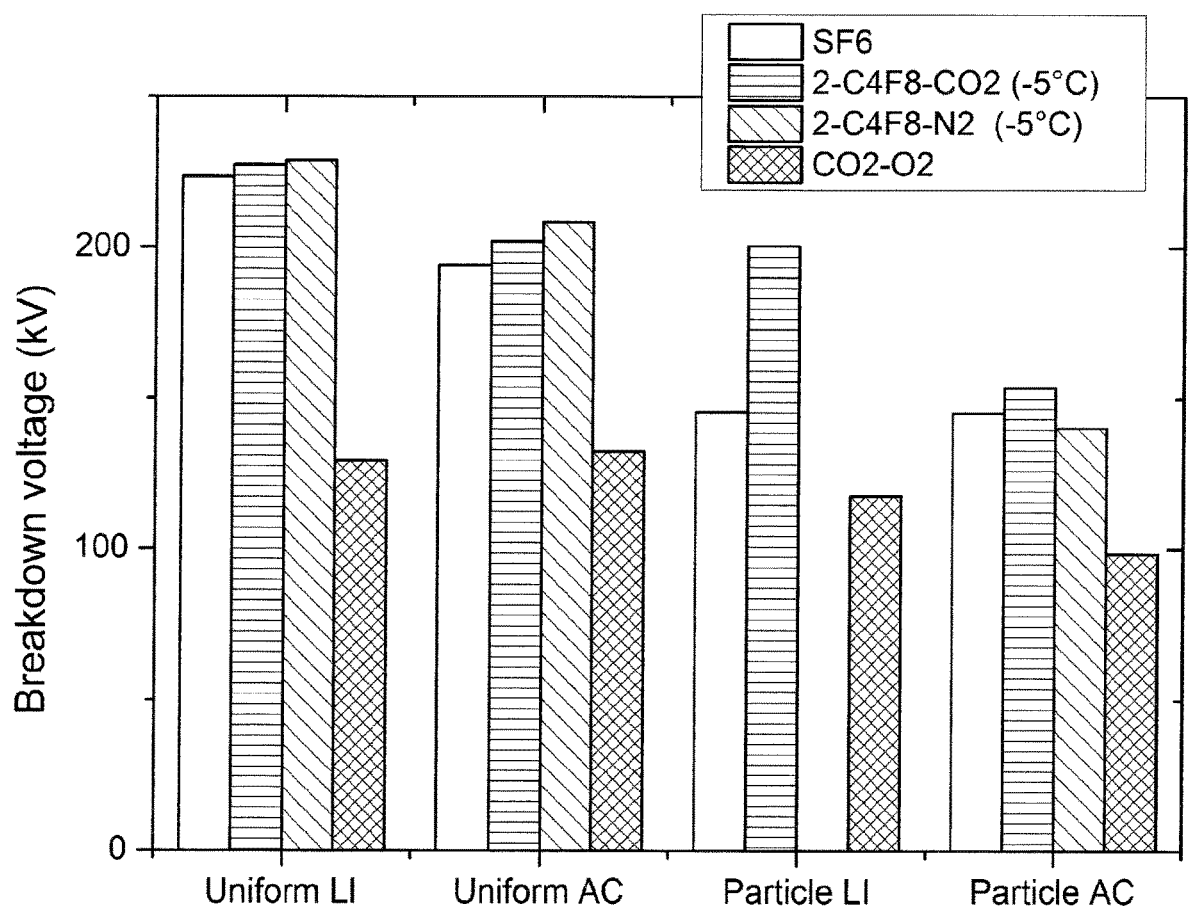

USE OF A LINEAR OCTAFLUOROBUTENE AS A DIELECTRIC COMPOUND IN AN ENVIRONMENTALLY SAFE DIELECTRIC-INSULATION OR ARC-EXTINCTION FLUID

The present invention relates to the use of a linear octafluorobutene as a dielectric compound in an environmentally safe dielectric-insulation or arc-extinction fluid according to claim 1.

The invention further relates to a dielectric-insulation or arc-extinction fluid comprising or essentially consisting of a linear octafluorobutene as a first component A in mixture with a second component B different from the first component A according to claim 5, and to an apparatus for the generation, the transmission, the distribution and/or the usage of electrical energy according to claim 21.

Dielectric insulation media in gaseous or liquid state are conventionally applied for the insulation of an electrically conductive part in a wide variety of apparatuses, such as for example switchgears, gas-insulated substations (GIS), gas-insulated lines (GIL), transformers, and others, or electrical components, such as e.g. instrument transformers, tap changers, and others.

In medium or high voltage metal-encapsulated switchgears, for example, the electrically conductive part is arranged in a gas-tight housing, which defines an insulating space, said insulation space comprising an insulation gas and separating the housing from the electrically conductive part(s) without letting electrical current to pass through the insulation space. For interrupting the current in e.g. high voltage switchgears, the insulation gas further functions as an arc-extinction gas.

Sulphur hexafluoride ($SF_6$) is a well-established insulation gas due to its outstanding dielectric properties and its chemical inertness. Despite of these properties, efforts to look for an alternative insulation gas have nevertheless been intensified, in particular in view of a lower Global Warming Potential (GWP) than the one of $SF_6$.

Recently, the use of organofluorine compounds in dielectric insulation media has been suggested. Specifically, WO-A-2010/142346 discloses a dielectric insulation medium comprising a fluoroketone containing from 4 to 12 carbon atoms. Fluoroketones have been shown to have a high dielectric strength. At the same time, they have a very low GWP and very low toxicity. The combination of these characteristics renders these fluoroketones highly suitable as a possible alternative to conventional insulation gases.

Despite the high dielectric strength of the fluoroketones disclosed in WO-A-2010/142346, the insulation performance of the respective insulation medium can be limited due to the relatively low vapour pressure of the fluoroketone. This is particularly the case for applications in a low temperature environment. In these applications, only a relatively low partial pressure of the fluoroketone can be maintained without it becoming liquefied.

In consideration of these shortcomings, WO-A-2012/080246 suggests a dielectric insulation gas comprising a fluoroketone containing exactly 5 carbon atoms, in particular 1,1,1,3,4,4,4-heptafluoro-3-(trifluoromethyl)-butan-2-one (hereinafter referred to as "C5K"), in a mixture with a carrier gas, in particular air or an air component, which together with the fluoroketone provides a non-linear increase of the dielectric strength of the insulation medium over the sum of dielectric strengths of the gas components of the insulation medium.

Notwithstanding the excellent properties of the insulation medium according to WO-A-2012/080246, there is an ongoing interest in providing an alternative "non-$SF_6$" dielectric compound of lower boiling point in comparison to the above mentioned fluoroketones, thereby allowing for a higher concentration of the dielectric compound in the insulation gas. Ultimately, this shall allow for achieving an improved dielectric performance, also at relatively low operating temperatures.

In this regard, WO 2014/037566 suggests the use of a gaseous medium comprising heptafluoroisobutyronitrile in mixture with a diluting gas and thereby reports a boiling point of heptafluoroisobutyronitrile of $-3.9°$ C. at 1013 hPa. However, heptafluoroisobutyronitrile (hereinafter also referred to as "C4N") has the drawback of having a high impact on the environment; its atmospheric lifetime is about 11'000 days and its GWP is about 2'210, i.e. much higher than the respective values of C5K having an atmospheric lifetime of less than 20 days and a GWP of 1.

It has further been found that when used e.g. in a GIS, heptafluoroisobutyronitrile exhibits poor compatibility with the material of the GIS, which on the one hand affects the material getting into contact with the dielectric insulation or arc-extinction fluid. On the other hand, also the functionality of the insulation medium itself is affected due to decomposition of the heptafluoroisobutyronitrile contained therein.

In consideration of the above, the problem to be solved by the present invention is to provide a dielectric-insulation or arc-extinction fluid showing comparable dielectric performance than an insulation medium comprising heptafluoroisobutyronitrile, but which at the same time has a much lower impact on the environment.

In particular, the dielectric-insulation or arc-extinction fluid shall have a low GWP of less than 10.

In view of its use in an apparatus for the generation, the transmission, the distribution and/or the usage of electrical energy, and particularly in a GIS, the dielectric-insulation or arc-extinction fluid shall also exhibit an improved compatibility with the material of the apparatus in comparison to the material compatibility of an insulation medium comprising heptafluoroisobutyronitrile.

The problem is solved by the subject matter of the independent claims. Further or preferred embodiments of the invention are defined in the dependent claims.

According to claim 1, a linear octafluorobutene is used as a dielectric compound in a dielectric-insulation or arc-extinction fluid for an apparatus for the generation, the transmission, the distribution and/or the usage of electrical energy.

It has surprisingly been found, that by the use of a linear octafluorobutene an environmentally safe dielectric insulation fluid and specifically arc-extinction fluid is achieved.

The term "fluid" (used in the term "dielectric insulation fluid or arc-extinction fluid") relates to any fluid and particularly encompasses liquids, gases as well as two-phase systems comprising both a gaseous and a liquid phase.

In the context of the present invention, the term "environmentally safe" has the meaning of being non-ozone depleting and having a Global Warming Potential over a time horizon of 100 years of less than 10. Specifically, the present invention, thus, relates to the use of a linear octafluorobutene as a dielectric compound in a non-ozone depleting dielectric-insulation or arc-extinction fluid having a Global Warming Potential over a time horizon of 100 years of less than 10.

Specifically, the term "environmentally safe" also means that the dielectric-insulation or arc-extinction fluid has a relatively low toxicity level. More specifically, the median lethal dose (LC50; lethal concentration 50%; measured on rats) of the dielectric compound used in the environmentally safe dielectric-insulation or arc-extinction fluid is higher than 4'000 ppm, preferably higher than 5'000 ppm and more preferably higher than 6'000 ppm. Thus, the dielectric compound used according to the present invention ranges within the same toxicity class as previously mentioned C4N (having a much higher GWP than the dielectric compound used according to the present invention) and C5K (having a much higher boiling point than the dielectric compound used according to the present invention).

In addition to their surprisingly high environmental compatibility, linear octafluorobutenes have been found to have a relatively high dielectric strength. In uniform field conditions (using Rogowski profile electrodes with a technical surface having a roughness $R_z$ of 40 μm at a gap distance of 1 cm), the breakdown voltage of 500 mbar of a mixture of trans- and cis-octafluorobut-2-ene (in a weight ratio of about 3:1) was shown to be 68 kV, corresponding to a critical field of around 135±10 kV/(cm bar). This value is higher than the critical field of $SF_6$ [88 kV/(cm bar)] which emphasizes the potential of linear octafluorobutenes for an alternative "non-$SF_6$" insulation or arc-extinction fluid.

The high dielectric withstand achievable by using a linear octafluorobutene is further based on the relatively low boiling point of the compound, which allows a relatively high gas density to be achieved. In particular, the boiling point of the linear octafluorobutenes according to the present invention is much lower than e.g. the boiling point of 1,1,1,4,4,4-hexafluoro-2-butene described in DE 10 2014 220 985.

Linear octafluorobutenes are perfluorinated butenes of sum formula $C_4F_8$. There are three isomers of linear octafluoro-butenes, namely octafluorobut-1-ene, cis-octafluorobut-2-ene and trans-octafluorobut-2-ene. Currently, linear octafluorobutenes are not used in industrial scale and are predominantly used as precursors in organic chemistry.

In teaching the use of a linear octafluorobutene, the present invention is also in clear distinction from U.S. Pat. No. 4,175,048, which teaches a gaseous insulator to be used, comprising a first compound, which i.a. can be iso-perfluorobutene (i.e. a branched fluorobutene), and a second component selected from the group of $SF_6$, $N_2$, CO, $CO_2$, $H_2$, $C_3F_8$, $C_6F_6$ and mixtures thereof. A similar reasoning applies with regard to U.S. Pat. No. 4,257,905, which reports on the breakdown strength of cyclic $C_4F_8$ (c-$C_4F_8$) and iso-$C_4F_8$, both falling outside the definition of a linear octafluorobutene.

In fact, by teaching the use of linear octafluorobutene the present invention goes into a different direction than the teaching of e.g. GB 525,244, which nowhere discloses a linear octafluorobutene, but teaches compounds of general formula $C_nF_{2n+2}$ to be preferred.

The applicability of linear octafluorobutenes for achieving an environmentally safe insulation or arc-extinction medium is most surprising, since alkenes generally undergo addition reactions and are thus typically not envisaged for applications where a high inertness of the compound is of paramount importance. Also, alkenes are generally flammable in air, which led to the misconception in the technical field that fluorinated alkenes are in general not suitable as a surrogate for $SF_6$ in medium and high voltage applications, in which high safety standards have to be fulfilled. This misconception was further abetted by alkenes being known for their reactivity which also often manifests itself in toxicity.

Further, an LC50 at 4 h was erroneously reported to be at 81 ppm by the Toxicology Data Network (TOXNET) of the U.S. National Library of Medicine, which further acted detrimentally to the overall evaluation of the compound for its potential applicability in fields where high safety standards have to be complied with.

In consideration of the general doctrine regarding alkenes in general, and linear octafluorobutenes in specific, it is therefore most surprising that linear octafluorobutenes not only exhibit a relatively low GWP of 1 at most (for octafluorobut-1-ene) and of 6 at most (for octafluorobut-2-ene) over a time horizon of 100 years, but that it is also non-flammable and ranges within the same toxicity class as for example heptafluoroisobutyronitrile (C4N) and 1,1,1,3,4,4,4-heptafluoro-3-(trifluoromethyl)-butan-2-one (C5K).

It has further surprisingly been found that the octafluorobutene-containing fluid is inert, i.e. non-reactive, towards the material of the apparatus, with which the fluid gets into direct contact during its use in the apparatus. Thus, the insulation or arc-extinction composition exhibits a high material compatibility and remains its functionality also when used in the apparatus over a long period of time. Specifically, the material compatibility is highly improved in comparison to the material compatibility of an insulation medium containing heptafluoroisobutyronitrile.

Without wanting to be bound by the theory, it is assumed that the reactivity of the double bond of octafluorobutene towards electrophiles is substantially reduced by the electron drawing effect of the fluorine substituents. This has been confirmed by compatibility tests on multiple materials that are typically used in a gas insulated switchgear (GIS), such as Cu/Al plates, EPDM sealings, zeolites, $SiO_2$, paints, grease, nitrile-butadiene rubber, butyl rubber and specifically isobuten-isopren-rubber (IIR) or chlorobutyl-rubber (CIIR) or brombutyl-rubber (BIIR), and the like, as will be discussed in the context of the examples mentioned below.

Further, the dielectric-insulation medium can be used with a conventional adsorber, primarily designed to remove water and impurities from the insulation space, without facing the problem of the octafluorobutene being adsorbed by the adsorber. Specifically, a 5 Å zeolite can be used for desiccation of the insulation space, as there is no or only negligible adsorption of the octafluorobutene having an estimated kinetic diameter of about 6 Å. Ultimately, the functionality of the insulation or arc-extinction composition can be maintained over a long period of time, both for the reasons that by the removal of water decomposition reactions of the octafluorobutene are efficiently suppressed and that no or only a negligible amount of octafluorobutene is withdrawn from the composition by adsorption.

Apart from the use described above, the present invention further relates to a dielectric-insulation or arc-extinction fluid for an apparatus for the generation, the transmission, the distribution and/or the usage of electrical energy, the fluid comprising or essentially consisting of:
a) a linear octafluorobutene as a first component A in mixture with
b) a second component B different from the first component A, the proportion of the first component A in the dielectric-insulation or arc-extinction fluid being at least 3%.

The dielectric-insulation or arc-extinction fluid is, therefore, in further distinction from the article of A. Chachereau, C. M. Franck ($32^{nd}$ ICPIG, Jul. 26-31, 2015, Iasi, Romania "Electron swarm parameter measurements of perfluorobut-2-ene (2-C4F8)", which—apart from being silent regarding a dielectric-insulation or arc-extinction fluid that is environmentally safe—only discloses very diluted mixtures of less than 0.04 perfluorobut-2-ene.

If the dielectric-insulation or arc-extinction fluid is in the form of a gas, the term "proportion" used in this context relates to the percentage of the partial pressure of the first component A in relation to the total pressure of the dielectric-insulation or arc-extinction gas. Thus, for an application, in which the total pressure of the gas is 10 bar, a proportion of 3% of the first component A corresponds to a partial pressure of 300 mbar.

Due to the high dielectric withstand strength (or dielectric breakdown strength or breakdown field strength) of linear octafluorobutenes, the dielectric-insulation or arc-extinction medium defined above exhibits a good dielectric performance at relatively moderate filling pressures of the apparatus.

In order to ensure that a relatively high fraction of component A, in particular of octafluorobut-2-ene, is in gaseous state at operational conditions, the fluid has on the one hand preferably a dew point below a pre-determined threshold temperature, particularly below the minimum operating temperature of the apparatus. On the other hand, a relatively high partial pressure of component A is desired for achieving a high gas density of said component and, hence, a high dielectric withstand strength.

According to embodiments, the dielectric-insulation or arc-extinction fluid has a dew point of lower than $-20°$ C., wherein the partial pressure of component A, in particular octafluorobut-2-ene, (as measured at 293.15 K) is higher than 250 mbar, preferably higher than 380 mbar; or the dielectric-insulation or arc-extinction fluid has a dew point of lower than $-25°$ C., wherein the partial pressure of component A, in particular octafluorobut-2-ene (as measured at 293.15 K) is higher than 150 mbar, preferably higher than 325 mbar. According to these embodiments, a relatively high gas density of the first component A can be obtained, which is still low enough to ensure a dew point of lower than $-20°$ C. or $-25°$ C., respectively, ultimately allowing for an optimal dielectric withstand strength also for apparatuses having a minimum operating temperature of $-20°$ C. or $-25°$ C., respectively.

Depending on the application, a higher dew point can be acceptable, allowing for a higher proportion of component A, in particular octafluorobut-2-ene, in the fluid. According to further preferred embodiments, the dielectric-insulation or arc-extinction fluid, thus, has a dew point of lower than $0°$ C., wherein the partial pressure of component A, in particular octafluorobut-2-ene (as measured at 293.15 K) is higher than 800 mbar, preferably higher than 900 mbar; or the dielectric-insulation or arc-extinction fluid, thus, has a dew point of lower than $-5°$ C., wherein the partial pressure of component A, in particular octafluorobut-2-ene (as measured at 293.15 K) is higher than 750 mbar, preferably higher than 850 mbar.

According to embodiments, the total pressure is higher than 6 bar when measured at 293.15 K, in order to obtain a particularly high dielectric withstand strength.

At 6 bar filling pressure of the apparatus, for example, a mixture of octafluorobutene with $N_2$ at $-25°$ C. has been found to have a dielectric withstand strength corresponding to about 93% of the dielectric withstand of a mixture of heptafluoroisobutyronitrile with $O_2$ and $CO_2$, the latter mixture being, however, unsuitable from an ecological point of view, as mentioned above.

At 8 bar filling pressure, a mixture of octafluorobutene with $CO_2$ has been found to have almost the same dielectric withstand strength than a mixture of heptafluoroisobutyronitrile and $CO_2$ at 6 bar filling pressure. Specifically, the measured dielectric withstand of the octafluorobutene/$CO_2$ mixture at 8 bar filling pressure corresponded to 95% of the dielectric withstand strength of the heptafluoroisobutyronitrile/$CO_2$ mixture at 6 bar filling pressure.

In comparison to heptafluoroisobutyronitrile-containing media, the dielectric-insulation fluid of the present invention therefore allows to achieve comparable dielectric performance at slightly increased filling pressures, but at a much higher ecological safety level, in particular at a much lower GWP.

With regard to the minimum operating temperature of the apparatus in which the fluid of the present invention is to be used, a dielectric performance (in particular dielectric withstand or breakdown strength) comparable to the one of a heptafluoroisobutyronitrile containing medium can—at the same filling pressure—be achieved at a slightly increased operating temperature, again at a much higher ecological safety level, as discussed above. In comparison to a heptafluoroisobutyronitrile containing medium at an operating temperature of $-25°$ C., for example, a decrease of 99% in GWP can be achieved by the present invention for the same level of dielectric performance at an operating temperature of $-5°$ C. Thus, for indoor applications, which according to standard IEC 62271-203:2011 have a minimum operating temperature of $-5°$ C., a high dielectric performance can be achieved by using the fluid of the present invention while simultaneously ensuring a high environmental safety.

In view of its use as an alternative for $SF_6$, the dielectric-insulation or arc extinction medium of the present invention allows to achieve a breakdown voltage (or dielectric withstand or breakdown strength) at $-5°$ C. at 7 bar, which can more or less replace 4.5 bar of $SF_6$. Thus, the same dielectric performance as for a $SF_6$ can be achieved at a pressure, which can in most cases be withstood by the housing (or encapsulation) walls of the apparatus.

Throughout this application and unless noted otherwise, all references to a pressure in the context of the present invention refer to the pressure measured at 293.15 K.

Specifically, the partial pressure of the linear octafluorobutene, in particular of the octafluorobut-2-ene, is such that the dew point of the dielectric-insulation or arc-extinction fluid is below the minimum operating temperature of the apparatus, thus ensuring that a high fraction of the octafluorobutene is in gaseous phase at operating conditions of the apparatus, as mentioned above. The dielectric-insulation or arc-extinction fluid has thus preferably a dew point of lower than $5°$ C., preferably lower than $0°$ C., more preferably lower than $-5°$ C., more preferably lower than $-20°$ C., and most preferably lower than $-25°$ C. (Herein, "temperature lower than" means colder temperature). Since the most common operating temperatures of electrical apparatuses are $-25°$ C., $-15°$ C., $-5°$ C. and $+5°$ C., the present invention allows a dielectric-insulation or arc-extinction fluid to be provided, which qualifies for all indoor applications and most of the outdoor applications, if not all of the outdoor applications.

According a further embodiments, the first component A is octafluorobut-1-ene or octafluorobut-2-ene, in particular octafluorobut-2-ene, and more particularly is the transisomer of octafluorobut-2-ene. The preference of octafluoro-but-1-ene or octafluorobut-2-ene is depending on the respective application and the specific aim to be achieved, given the finding that octafluorobut-1-ene has a GWP of 1 and thus a slightly lower GWP than octafluorobut-2-ene (having a GWP of 6), but a measured dielectric withstand strength that is about 15% lower than the one of octafluorobut-2-ene. The trans-isomer of octafluorobut-2-ene can be preferred in applications where a molecular sieve is present, since by the greater kinetic diameter the trans-isomer is less prone for adsorption by the molecular sieve than the cis-isomer. This will be discussed in more detail by way of the examples below, where tests were performed in an environment in which a zeolite having a pore size of 5 Å was contained.

In general embodiments of the dielectric-insulation or arc-extinction fluid or apparatus for the generation, transmission, distribution and/or usage of electrical energy having a desired dew point or minimum operating temperature lower than 0° C., the partial pressure of component A, in particular octafluorobut-2-ene, as measured at 293.15 K shall be chosen lower than 1100 mbar.

In general embodiments of the dielectric-insulation or arc-extinction fluid or apparatus for the generation, transmission, distribution and/or usage of electrical energy having a desired dew point or minimum operating temperature lower than −5° C., the partial pressure of component A, in particular octafluorobut-2-ene, as measured at 293.15 K shall be chosen lower than 950 mbar.

In general embodiments of the dielectric-insulation or arc-extinction fluid or apparatus for the generation, transmission, distribution and/or usage of electrical energy having a desired dew point or minimum operating temperature lower than −20° C. or −25° C., respectively, the partial pressure of component A, in particular octafluorobut-2-ene, as measured at 293.15 K shall be chosen lower than 520 mbar or 420 mbar, respectively.

In further general embodiments of the dielectric-insulation or arc-extinction fluid or apparatus for the generation, transmission, distribution and/or usage of electrical energy, in order to achieve high dielectric strength and at the same time to avoid condensation, the partial pressure of component A, in particular octafluorobut-2-ene, shall be chosen in a range of 800 mbar to 1100 mbar, particularly 900 mbar to 1100 mbar, to maintain a dew point or minimum operating temperature of 0° C.; or shall be chosen in a range of 750 mbar to 950 mbar, particularly 850 mbar to 950 mbar, to maintain a dew point or minimum operating temperature of −5° C.; or shall be chosen in a range of 250 mbar to 520 mbar, particularly 380 mbar to 520 mbar, to maintain a dew point or minimum operating temperature of −20° C.; or shall be chosen in a range of 150 mbar to 420 mbar, particularly 325 mbar to 420 mbar, to maintain a dew point or minimum operating temperature of −25° C.

In order to achieve a high enough gas density for achieving the desired dielectric performance, the second component B preferably comprises or essentially consists of a carrier gas, which has a boiling point of −60° C. at most. It is further preferred that the second component B comprises or essentially consists of a carrier gas, which itself has a lower dielectric strength than the first component A. According to a still further embodiments, the second fluid component B comprises or consists of a carrier gas selected from the group consisting of: oxygen, nitrogen, carbon dioxide, nitrous oxide, and mixtures thereof.

In particular embodiments, the second fluid component B comprises or consists of carbon dioxide and/or of nitrogen.

In this regard it can be further preferred that the second fluid component B further comprises oxygen. A second fluid component B comprising oxygen (apart from carbon dioxide and/or nitrogen) is preferred in view of applications wherein soot might be formed, since soot formation is efficiently prevented by the presence of oxygen. This applies in particular to the use of the dielectric insulation medium as arc-extinction fluid in a circuit breaker, more particularly in a high voltage circuit breaker.

In specific embodiments, the second fluid component B comprises or consists of a mixture of carbon dioxide and oxygen or of a mixture of nitrogen and oxygen.

In more concrete terms, the second fluid component B can thus be
carbon dioxide;
nitrogen;
a mixture of oxygen and carbon dioxide;
a mixture of oxygen and nitrogen; and
a mixture of oxygen, nitrogen and carbon dioxide.

It has been found that by oxygen being present in the insulation or arc-extinction fluid of the present invention, the risk of formation of highly toxic gases by partial discharge can substantially be reduced.

It has further been found that the content of oxygen in the insulation or arc-extinction fluid does not significantly affect the dielectric withstand of the fluid. Thus, the $O_2$ content in the fluid can be more or less freely adjusted, in order to decrease the formation rate of toxic decomposition products, such as PFIB, or to fulfil other constraints.

According to a preferred embodiment, the second fluid component B thus comprises oxygen. Ultimately, this allows the good dielectric performance of the insulation or arc-extinction fluid as well as its very low toxicity to be maintained over a long period of use.

By the second fluid component B comprising oxygen, the dielectric-insulation or arc-extinction fluid of this specific embodiment of the present invention is in even clearer distinction from the article of Chachereau et al. mentioned above, which only discloses low-concentration mixtures of perfluorobut-2-ene with $N_2$, $CO_2$ and Argon.

A second fluid component B being a mixture of oxygen and carbon dioxide is particularly preferred. Depending on the application, it can in this context be further preferred that the $O_2/CO_2$ mixture additionally contains nitrogen, more preferably in a proportion of less than 20% based on the total pressure of the second fluid component B. The presence of nitrogen is preferred in view of obtaining a high dielectric strength (dielectric withstand or breakdown strength or voltage) of the medium in which it is contained, since nitrogen is able to slow down electrons efficiently. In particular in view of the fluids use in a switching apparatus, a restriction of the nitrogen content to 20% can be preferred, since a higher nitrogen content might lead to a reduction of the arc-extinguishing capabilities of the fluids.

In a further preferred embodiment, which in particular relates to the case that the fluid is an insulation fluid serving purely for the purpose of dielectric insulation, the second fluid component B is a mixture of oxygen and nitrogen.

In an alternative preferred embodiment, which in particular relates to the case that the fluid is an arc-extinction fluid, the second fluid component B comprises carbon dioxide, optionally in a mixture which oxygen, which preferably is contained in a lower amount than the carbon oxide.

According to further embodiments, the dielectric-insulation or arc-extinction fluid comprises a linear octafluorobutene as dielectric compound in combination with carbon dioxide as carrier gas. This mixture provides both a high thermal performance (i.e. arc-extinction performance or arc-extinction strength) due to the use of carbon dioxide, and a high dielectric performance due to the use of the linear octafluorobutene.

According to still further embodiments, the dielectric-insulation or arc-extinction fluid comprises as the second fluid component B or as a third fluid component C a further fluorinated organic compound different from the linear octafluorobutene of the first gas component. In this regard, it is further preferred that the further fluorinated organic compound is at least one compound selected from the group consisting of: fluoroethers, in particular hydrofluoromonoethers, fluoroketones, in particular perfluoroketones, fluoroolefins other than a linear octafluorobutene, in particular hydrofluoroolefins, and fluoronitriles, in particular perfluoronitriles, and mixtures thereof.

With regard to this embodiment, it is particularly preferred that the further fluorinated organic compound is a fluoroketone containing from four to twelve carbon atoms, preferably containing exactly five carbon atoms or exactly six carbon atoms or mixtures thereof.

The term "fluoroketone" as used in this application shall be interpreted broadly and shall encompass both perfluoroketones and hydrofluoroketones, and shall further encompass both saturated compounds and unsaturated compounds, i.e. compounds including double and/or triple bonds between carbon atoms. The at least partially fluorinated alkyl chain of the fluoroketones can be linear or branched, or can form a ring, which optionally is substituted by one or more alkyl groups. In exemplary embodiments, the fluoroketone is a perfluoroketone. In further exemplary embodiments, the fluoroketone has a branched alkyl chain, in particular an at least partially fluorinated alkyl chain. In still further exemplary embodiments, the fluoroketone is a fully saturated compound.

As mentioned, it is particularly preferred that the further fluorinated organic compound is a fluoroketone containing exactly five carbon atoms, in particular 1,1,1,3,4,4,4-heptafluoro-3-(trifluoromethyl)-butan-2-one (also named decafluoro-3-methylbutan-2-one; herein referred to as "C5K"), or exactly six carbon atoms, in particular 1,1,1,2,4,4,5,5,5-Nonafluoro-2-(trifluoromethyl)pentan-3-one (also named dodecafluoro-2-methylpentan-3-one), or mixtures thereof. Compared to fluoroketones having a greater chain length with more than six carbon atoms, fluoroketones containing five or six carbon atoms have the advantage of a relatively low boiling point. Thus, problems which might go along with liquefaction can be avoided, even when the apparatus is used at low temperatures.

In additional or alternative embodiments, the further fluorinated organic compound is a hydrofluoroether selected from the group consisting of: hydrofluoro monoether containing at least three carbon atoms; hydrofluoro monoether containing exactly three or exactly four carbon atoms; hydrofluoro monoether having a ratio of number of fluorine atoms to total number of fluorine and hydrogen atoms of at least 5:8; hydrofluoro monoether having a ratio of number of fluorine atoms to number of carbon atoms ranging from 1.5:1 to 2:1; pentafluoro-ethyl-methyl ether; 2,2,2-trifluoroethyltrifluoromethyl ether; and mixtures thereof.

The further fluorinated organic compound can also be a fluoroolefin other than a linear octafluorobutene, in particular a hydrofluoroolefin. More particularly, the fluoroolefin or hydrofluoroolefin, respectively, contains at least three carbon atoms or contains exactly three carbon atoms.

According to further embodiments, the hydrofluoroolefin is thus selected from the group consisting of: 1,1,1,2-tetrafluoropropene (HFO-1234yf; also named 2,3,3,3-tetrafluoro-1-propene), 1,2,3,3-tetrafluoro-2-propene (HFO-1234yc), 1,1,3,3-tetrafluoro-2-propene (HFO-1234zc), 1,1,3-tetrafluoro-2-propene (HFO-1234ze), 1,1,2,3-tetrafluoro-2-propene (HFO-1234ye), 1,1,2,3-pentafluoropropene (HFO-1225ye), 1,2,3,3-pentafluoropropene (HFO-1225yc), 1,1,1,3,3-pentafluoropropene (HFO-1225zc), (Z)1,1,1,3-tetrafluoropropene (HFO-1234zeZ); also named cis-1,3,3,3-tetrafluoro-1-propene), (Z)1,1,2,3-tetrafluoro-2-propene (HFO-1234yeZ), (E)1,1,1,3-tetrafluoropropene (HFO-1234zeE; also named trans-1,3,3,3-tetrafluoro-1-propene), (E)1,1,2,3-tetrafluoro-2-propene (HFO-1234yeE), (Z)1,1,1, 2,3-pentafluoropropene (HFO-1225yeZ; also named cis-1, 2,3,3,3 pentafluoroprop-1-ene), (E)1,1,1,2,3-pentafluoropropene (HFO-1225yeE; also named trans-1,2,3,3,3 pentafluoroprop-1-ene); and mixtures thereof.

As mentioned above, the further fluorinated organic compound can also be a fluoronitrile, in particular a perfluoronitrile, despite of its relatively poor environmental safety. In particular, the organofluorine compound can be a fluoronitrile, specifically a perfluoronitrile, containing two carbon atoms, three carbon atoms or four carbon atoms.

More particularly, the fluoronitrile can be a perfluoroalkylnitrile, specifically perfluoroacetonitrile, perfluoropropionitrile ($C_2F_5CN$) and/or perfluorobutyronitrile ($C_3F_7CN$). Most particularly, the fluoronitrile can be perfluoroisobutyronitrile (according to the formula $(CF_3)_2CFCN$) and/or perfluoro-2-methoxypropanenitrile (according to the formula $CF_3CF(OCF_3)CN$). Of these, perfluoroisobutyronitrile is particularly preferred due to its relatively low toxicity.

Apart from the use and the fluid described above, the present invention further relates to an apparatus for the generation, the transmission, the distribution and/or the usage of electrical energy, said apparatus comprising a housing enclosing an insulating space and an electrically conductive part arranged in the insulating space, wherein said insulating space contains a dielectric-insulation or arc-extinction fluid, in particular dielectric-insulation or arc-extinction gas, comprising or essentially consisting of:
 a) a first gas component A comprising or essentially consisting of a linear octafluorobutene, in mixture with
 b) a second gas component B different from the first gas component A,
and having at operating conditions a pressure higher than 1 bar.

Specifically, the preferred features of the dielectric-insulation or arc-extinction fluid presented above likewise apply to the dielectric-insulation or arc-extinction fluid of the apparatus of the present invention. In particular, the dielectric-insulation or arc-extinction fluid is a dielectric-insulation or arc-extinction gas.

If the apparatus is a high voltage apparatus, the pressure is preferably higher than 3 bar, more preferably higher than 4 bar and most preferably higher than 4.5 bar at operating conditions.

If the apparatus is a medium voltage apparatus, the pressure can be lower and preferably is in a range from 1 bar to 2 bar, most preferably from 1.3 bar to 1.4 bar, at operating conditions.

It has been found that for this operating pressure, a sufficiently high dielectric withstand can be achieved also when the minimum operating temperature is relatively low. The apparatus of the present invention thus specifically relates to an apparatus having a rated minimal operating temperature of at least −25° C., preferably at least −15° C., most preferably at least −5° C. (Herein, "at least a temperature" means this temperature or a warmer temperature).

Particularly, the apparatus is a medium voltage or a high voltage apparatus, and more particularly is or is part of a: switchgear, in particular gas-insulated switchgear (GIS), or part and/or component thereof, gas-insulated line (GIL), busbar, bushing, cable, gas-insulated cable, cable joint, current transformer, voltage transformer, sensor, humidity sensor, surge arrester, capacitor, inductance, resistor, insulator, air-insulated insulator, a gas-insulated metal-encapsulated insulator, current limiter, high voltage switch, earthing switch, disconnector, combined disconnector and earthing switch, load-break switch, circuit breaker, gas circuit breaker, generator circuit breaker, gas-insulated vacuum circuit breaker, medium voltage switch, ring main unit, recloser, sectionalizer, low voltage switch, and/or any type of gas-insulated switch, transformer, distribution transformer, power transformer, tap changer, transformer bushing, electrical rotating machine, generator, motor, drive, semiconducting device, computing machine, power semiconductor device, power converter, converter station, convertor building, and components and/or combinations of such devices.

The advantages achievable by the present invention are particularly apparent in switching applications, in particular in a circuit breaker. In this regard, it has surprisingly been found that by the presence of octafluorobutene, specifically trans-octafluorobut-2-ene, the dielectric-insulation or arc-extinction fluid of the present invention allows—apart from the advantages mentioned above—also a faster dielectric recovery to be achieved, when compared to e.g. pure $CO_2$. Thus, the speed at which the hot gas in a circuit breaker regains its dielectric withstand after the interruption of the current can be increased according to the present invention.

As mentioned above, the term dielectric-insulation fluid also encompasses a dielectric-insulation liquid. In this context, the use of a linear octafluorobutene in a dielectric-insulation liquid for a transformer is specifically mentioned.

As mentioned above, the advantages of the present invention are particularly apparent for indoor applications, which according to standard IEC 62271-203:2011 have a minimum operating temperature of −5° C. According to a particularly preferred embodiment, the apparatus of the present invention is therefore preferably designed for an indoor application.

As mentioned above, the insulation or arc-extinction fluid exhibits a high material compatibility and remains its functionality also when used in the apparatus over a long period of time. In this regard, the present invention is of particular relevance when at least some of the solid components of the apparatus that are directly exposed to the insulation gas, are made of a polymeric material, a metal, a metal alloy, a ceramic and/or a composite thereof.

A high material compatibility is in particular also given, if the polymeric material is selected from the group consisting of: silicones, polyolefins, polyethers, polyesters, polyurethanes, polyepoxides, polyamides, polyimides, polyketones, polysulfones, as well as mixtures or combinations thereof.

In particular, the above mentioned component towards which the fluid of the present invention exhibits a high compatibility, may be selected from the group consisting of: a coating compound, in particular a paint or a resin, a sealing compound, an adhesive, an insulating compound, a lubricating compound, in particular grease, a molecular sieve, a binder-free molecular sieve, a desiccant, a binder-free desiccant, a humidity sensing material, as well as mixtures thereof.

EXAMPLES

Decomposition Tests

In order to assess the material compatibility of octafluoro-2-butene towards material typically used in a GIS, the following components were aged at accelerated conditions (at 100° C.) with octafluoro-2-butene gas:
Cu/Al plates;
EPDM sealings;
Zeolites;
$SiO_2$;
Paints;
Grease; and
Nitrile-butadiene rubber.

Both the gas as well as the components exposed to the gas were analysed after 8 weeks of exposure. For none of the tests, a decomposition of the octafluoro-2-butene was determined. Also, the material of the components did not undergo decomposition and remained fully intact.

Adsorption Test

In addition to these tests, adsorption tests were performed in order to assess whether octafluoro-2-butene is adsorbed by zeolites (which can be used as molecular sieve for adsorbing water and/or decomposition products of the insulation gas). To this end, an autoclave was filled with a mixture of octafluoro-2-butene and nitrogen in the presence of zeolites of different pore size, specifically in a range from 3 Å to 5 Å.

Gas samples were analysed using GC (gas chromatography) after 1 day and the results were compared with analogous samples in the absence of zeolites. The results showed for the zeolite having a pore size of 3 Å, that no adsorption of octafluoro-2-butene takes place.

For the zeolite having a pore size of 5 Å, the trans-isomer was not adsorbed, while for the cis-isomer some adsorption was determined.

Dielectric Performance Tests

In order to assess the dielectric performance of the dielectric-insulation or arc-extinction fluid, the breakdown voltage at two different field conditions were measured under lightning impulse and under AC stress. Specifically, measurements were taken at uniform field conditions (Rogowski profile electrodes, technical surface (roughness: $R_z=25$ μm), 0.75 cm gap distance) as well as under particle-like field conditions, were a needle of 1.2 mm length was inserted within one of the electrodes.

The breakdown voltage under these conditions was determined for different insulation media, namely for $SF_6$ at 4.5 bar, for octafluoro-2-butene in mixture with $CO_2$ and $O_2$ (having a dew point of −5° C.) at 7 bar, for octafluoro-2-butene in mixture with $N_2$ and $O_2$ (having a dew point of −5° C.) at 7 bar and for a $CO_2/O_2$ mixture at 7 bar.

The results are summarized in

FIG. 1 showing the breakdown voltage at two different field conditions, each measured under lightning impulse (LI) and under AC stress (AC), for two dielectric-insulation fluids according to the present invention (at 7 bar) in comparison to $SF_6$ (at 4.5 bar) and a $CO_2/O_2$ mixture (at 7 bar).

According to FIG. 1, a slightly higher breakdown voltage was determined for the uniform field tests using the fluid according to the present invention compared with the one using $SF_6$, the highest values (of about 230 kV under lightning impulse and of about 210 kV under AC stress) having been determined for the octafluoro-2-butene/$N_2$ mixture.

For the particle-like field tests, the highest breakdown voltage was determined for the octafluoro-2-butene/$CO_2$ mixture, the value being at about 200 kV under lightning impulse and therefore much higher than the respective value determined for $SF_6$ (being lower than 150 kV).

Thus, the fluid according to the present invention allows to achieve a breakdown voltage (dielectric withstand or breakdown strength or breakdown field strength or breakdown voltage) at −5° C. at 7 bar, which equals or even surpasses the one measured for 4.5 bar of $SF_6$. Thus, the same dielectric performance as for $SF_6$ can be achieved at a pressure which can in most cases be withstood by conventional housing (or encapsulation) walls of the apparatus.

Throughout this application, "medium voltage" relates to voltages in the range of 1 kV to 52 kV or 72 kV, and "high voltage" to voltages above this range. While there are shown and described presently preferred embodiments of the invention, it is to be distinctly understood that the invention is not limited thereto but may otherwise variously be embodied and practised within the scope of the following claims. Therefore, terms like "preferred" or "in particular" or "particularly" or "advantageously", etc. signify optional and exemplary embodiments only.

The invention claimed is:

1. A combination, comprising:
a linear octafluorobutene utilized as a dielectric compound in an environmentally safe dielectric-insulation or arc-extinction fluid for an apparatus for the generation, the transmission, the distribution and/or the usage of electrical energy, wherein the proportion of the linear octafluorobutene dielectric compound in the dielectric-insulation or arc-extinction fluid is in a range from about 3% to less than 1%,
wherein the dielectric-insulation or arc-extinction fluid is free of $SF_6$, and
wherein the second component B comprises a carrier gas that comprises one of oxygen, nitrous oxide, a mixture of oxygen and carbon dioxide, a mixture of nitrogen and oxygen and a mixture of nitrous oxide and oxygen.

2. The combination according to claim 1, wherein the dielectric-insulation or arc-extinction fluid is non-ozone depleting and has a Global Warming Potential over a time horizon of 100 years of less than 10.

3. The combination according to claim 1, wherein the dielectric-insulation of arc-extinction fluid is inert towards the material of the apparatus, with which the fluid gets into direct contact during its use in the apparatus.

4. The combination according to claim 1, wherein the median lethal dose (LC50; lethal concentration 50%; measured on rats) of the dielectric compound is higher than 4'000 ppm.

5. The combination according to claim 1, wherein a second component of the dielectric-insulation or arc-extinction fluid comprises a carrier gas selected from the group consisting of: oxygen, nitrous oxide, and mixtures thereof.

6. The combination according to claim 5, wherein the second component of the dielectric-insulation or arc-extinction fluid further comprises a carrier gas comprising nitrogen, carbon dioxide, and mixtures thereof.

7. A dielectric-insulation or arc-extinction fluid for an apparatus for the generation, the transmission, the distribution and/or the usage of electrical energy, the fluid comprising:
a) a linear octafluorobutene as a first component A in mixture with
b) a second component B different from the first component A, the proportion of the first component A in the dielectric insulation of arc-extinction fluid being in a range from about 3% to less than 10%,
wherein the dielectric-insulation or arc-extinction fluid is free of $SF_6$, and
wherein the second component B comprises a carrier gas that comprises one of oxygen, nitrous oxide, a mixture of oxygen and carbon dioxide, a mixture of nitrogen and oxygen and a mixture of nitrous oxide and oxygen.

8. The dielectric-insulation or arc-extinction fluid according to claim 7, wherein the dew point is less than a minimum operating temperature corresponding to an indoor use of the apparatus.

9. The dielectric-insulation or arc-extinction fluid according to claim 7, having a dew point of lower than −20° C., wherein the partial pressure of component A as measured at 293.15 K is higher than 250 mbar; or
having a dew point of lower than −25° C., wherein the partial pressure of component A as measured at 293.15 K is higher than 150 mbar.

10. The dielectric-insulation or arc-extinction fluid according to claim 7, having a dew point of lower than 0° C., wherein the partial pressure of component A as measured at 293.15 K is higher than 900 mbar; or
having a dew point of lower than −5° C., wherein the partial pressure of component A as measured at 293.15 K is higher than 750 mbar.

11. The dielectric-insulation or arc-extinction fluid according to claim 7, the total pressure of which being at least 6 bar as measured at 293.15 K.

12. The dielectric-insulation or arc-extinction fluid according to claim 7, being non-ozone depleting and having a Global Warming Potential over a time horizon of 100 years of less than 10.

13. The dielectric-insulation or arc-extinction fluid according to claim 7, wherein the first component A is octafluorobut-1-ene or octafluorobut-2-ene.

14. The dielectric-insulation or arc-extinction fluid according to claim 7, wherein the second component B comprises a carrier gas, which has a boiling point of −60° C. at most.

15. The dielectric-insulation or arc-extinction fluid according to claim 7, wherein the second component B comprises a carrier gas, which itself has a lower dielectric strength than the first component A.

16. The dielectric-insulation or arc-extinction fluid according to claim 7, wherein the second fluid component B comprises a carrier gas selected from the group consisting of: oxygen, nitrogen, carbon dioxide, nitrous oxide, and mixtures thereof.

17. The dielectric-insulation or arc-extinction fluid according to claim 7, wherein the second fluid component B comprises carbon dioxide and/or nitrogen.

18. The dielectric-insulation or arc-extinction fluid according to claim 17, wherein the second fluid component B further comprises oxygen.

19. The dielectric-insulation or arc-extinction fluid according to claim 7, wherein the second fluid component B comprises a mixture of carbon dioxide and oxygen or of a mixture of nitrogen and oxygen or of a mixture of carbon dioxide and oxygen and nitrogen.

20. The dielectric-insulation or arc-extinction fluid according to claim 7, wherein it comprises as the second fluid component B or as a third fluid component C a further fluorinated organic compound different from the linear octafluorobutene of the first gas component A.

21. The dielectric-insulation or arc-extinction fluid according to claim 20, wherein the further fluorinated organic compound is at least one compound selected from the group consisting of: fluoroethers, fluoroketones, fluoroolefins other than a linear octafluorobutene, fluoronitriles, and mixtures thereof.

22. The dielectric-insulation or arc-extinction fluid according to claim 7, wherein the partial pressure of component A, as measured at 293.15 K is chosen in a range of 800 mbar to 1100 mbar; or
   in a range of 750 mbar to 950 mbar; or
   in a range of 250 mbar to 520 mbar; or in a range of 150 mbar to 420 mbar.

23. The dielectric-insulation or arc-extinction fluid according to claim 7, wherein the carrier gas further comprises at least one of nitrogen, carbon dioxide, and mixtures thereof.

* * * * *